DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED DECEMBER 2, 1975

941 O.G. 7

T941,010
ANTHELMINTIC METHOD OF TREATMENT
Jack Blodinger, 16 Bell Drive,
Westfield, N.J. 07090
Filed Feb. 15, 1974, Ser. No. 443,064
Int. Cl. A61k *27/00*
U.S. Cl. 424—217
No Drawing. 4 Pages Specification

A method for the treatment of helminths in mammals is disclosed whereby substantially concurrent administration 5-isopropoxycarbonylamino - 2 - thiazolyl benzimidazole and O,O-dimethyl-2,2,2-trichloro-1-hydroxy ethylphosphonate is effected.